US00PP34256P2

(12) United States Plant Patent
van Langen

(10) Patent No.: US PP34,256 P2
(45) Date of Patent: May 17, 2022

(54) ***ECHEVERIA* PLANT NAMED 'AMIECH2009'**

(50) Latin Name: ***Echeveria lilacina* x *E. parva.***
Varietal Denomination: AMIECH2009

(71) Applicant: Novoami B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 17/300,674

(22) Filed: Sep. 21, 2021

(30) Foreign Application Priority Data

Jan. 6, 2021 (QZ) ..... PBR 2021/0039

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373, 263.1
CPC ... A01H 5/12; A01H 5/02; A01H 5/00; A01H 6/32; A01H 6/00
See application file for complete search history.

*Primary Examiner* — June Hwu
(74) *Attorney, Agent, or Firm* — Samuel R. McCoy, Jr.

(57) ABSTRACT

A new and distinct *Echeveria* hybrid plant named 'AMIECH1009' which is characterized by flat, oblanceolate to narrowly obovate foliage with an obtuse to cuspidate apex, crenulate foliar margins that are slightly to moderately undulated, yellow-green mature foliage is prominently margined with a translucent light greyed-green color, strongly glaucous juvenile and mature foliage that is heavily covered with a layer of greyed-green epicuticular wax on both the adaxial and abaxial surfaces which gives the foliage a paled greyed-green appearance with a cyanic hue, and the stability of these characteristics from generation to generation.

4 Drawing Sheets

Latin name of the genus and species: The Latin name of the genus and species of the novel variety disclosed herein is *Echeveria lilacina* x *E. parva.*

Variety denomination: The inventive variety of *Echeveria* hybrid disclosed herein has been given the variety denomination 'AMIECH2009'.

CROSS REFERENCE TO RELATED APPLICATIONS

This application claims priority to the Community Plant Variety Rights application number 2021/0039, filed Jan. 6, 2021, which is herein incorporated by reference.

BACKGROUND OF THE INVENTION

Parentage: 'AMIECH2009' is an interspecific hybrid seedling selection resulting from the controlled pollination of an unnamed *Echeveria lilacina* plant (not patented), the seed parent, with an unnamed *Echeveria parva* plant (not patented), the pollen parent. The crossing was made by the inventor in the spring of 2016 at a commercial greenhouse in Heerhugowaard, the Netherlands. In the summer of 2017, one seedling was observed which exhibited unique growth and foliage characteristics. The seedling was isolated for further evaluation in order to confirm the distinctness and stability of the characteristics first observed. Upon confirmation of distinctness and stability, 'AMIECH2009' was selected for commercialization.

Asexual Reproduction: Asexual reproduction of the new cultivar 'AMIECH2009', by way of rooting leaf cuttings, was first initiated in the autumn of 2017 at the inventor's commercial greenhouse in Heerhugowaard, the Netherlands.

Through four subsequent generations, the unique features of this cultivar have proven to be stable and true to type.

SUMMARY OF THE INVENTION

The cultivar 'AMIECH2009' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2009'. These characteristics in combination distinguish 'AMIECH2009' as a new and distinct *Echeveria* hybrid cultivar:

1. 'AMIECH2009' exhibits a flattened to flattened globular plant profile with foliage somewhat loosely held in a basal rosette; and
2. 'AMIECH2009' exhibits flat, oblanceolate to narrowly obovate foliage with an obtuse to cuspidate apex; and
3. 'AMIECH2009' exhibits crenulate foliar margins that are slightly to moderately undulated; and
4. 'AMIECH2009' exhibits yellow-green mature foliage that is prominently margined with a translucent light greyed-green color; and
5. 'AMIECH2009' exhibits strongly glaucous juvenile and mature foliage that is heavily covered with a layer of greyed-green epicuticular wax on both the adaxial and abaxial surfaces which gives the foliage a pale greyed-green appearance with a cyanic hue.

BOTANICAL DESCRIPTION OF THE PLANT

Figure 1:
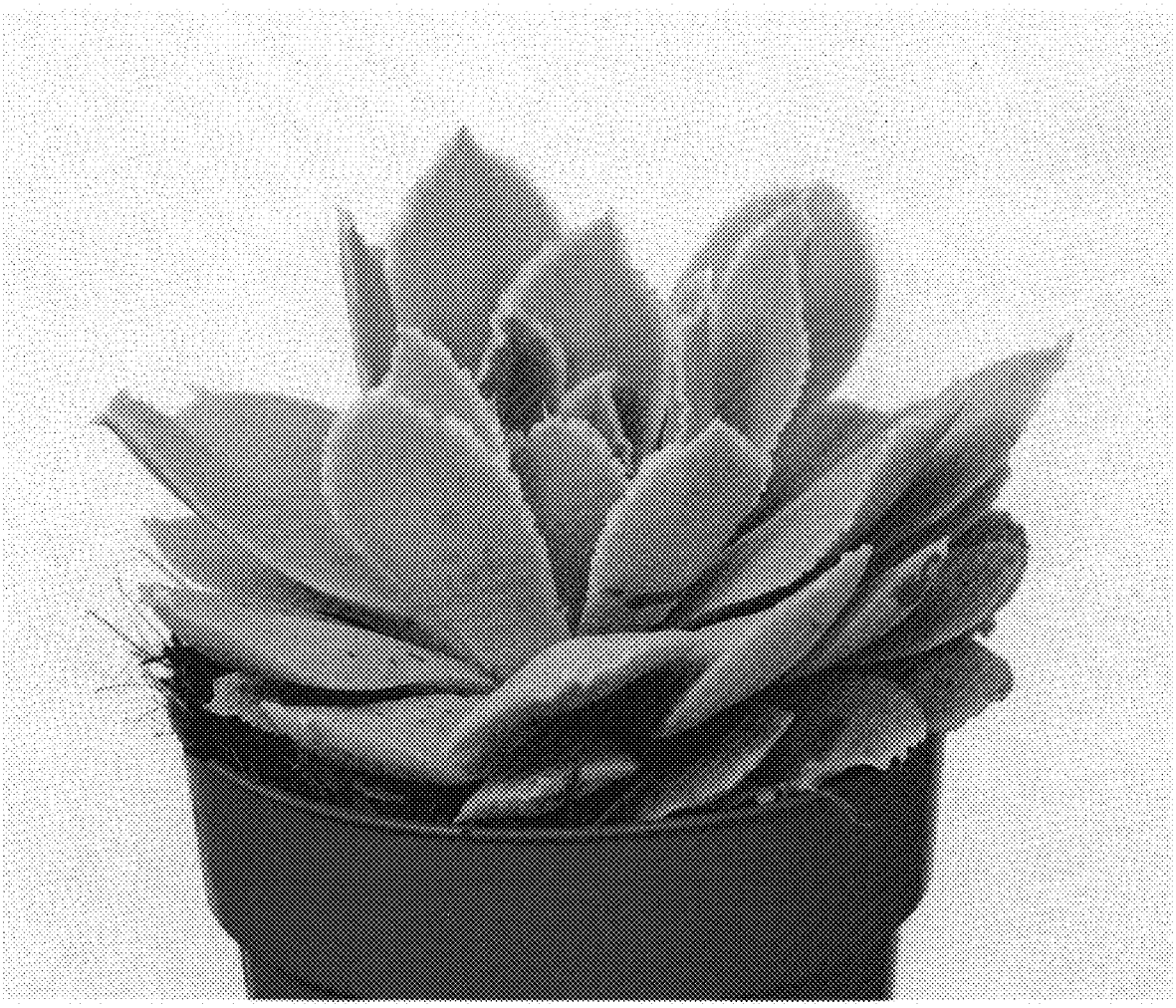
FIG. 1 illustrates, as nearly true as it is reasonably possible to make the same in color photographs of this type, an exemplary plant of 'AMIECH2009' grown in a commercial greenhouse in Heerhugowaard, the Netherlands. This plant is approximately 25 week-old, shown planted in an 8.5 cm container.
Figure 2:
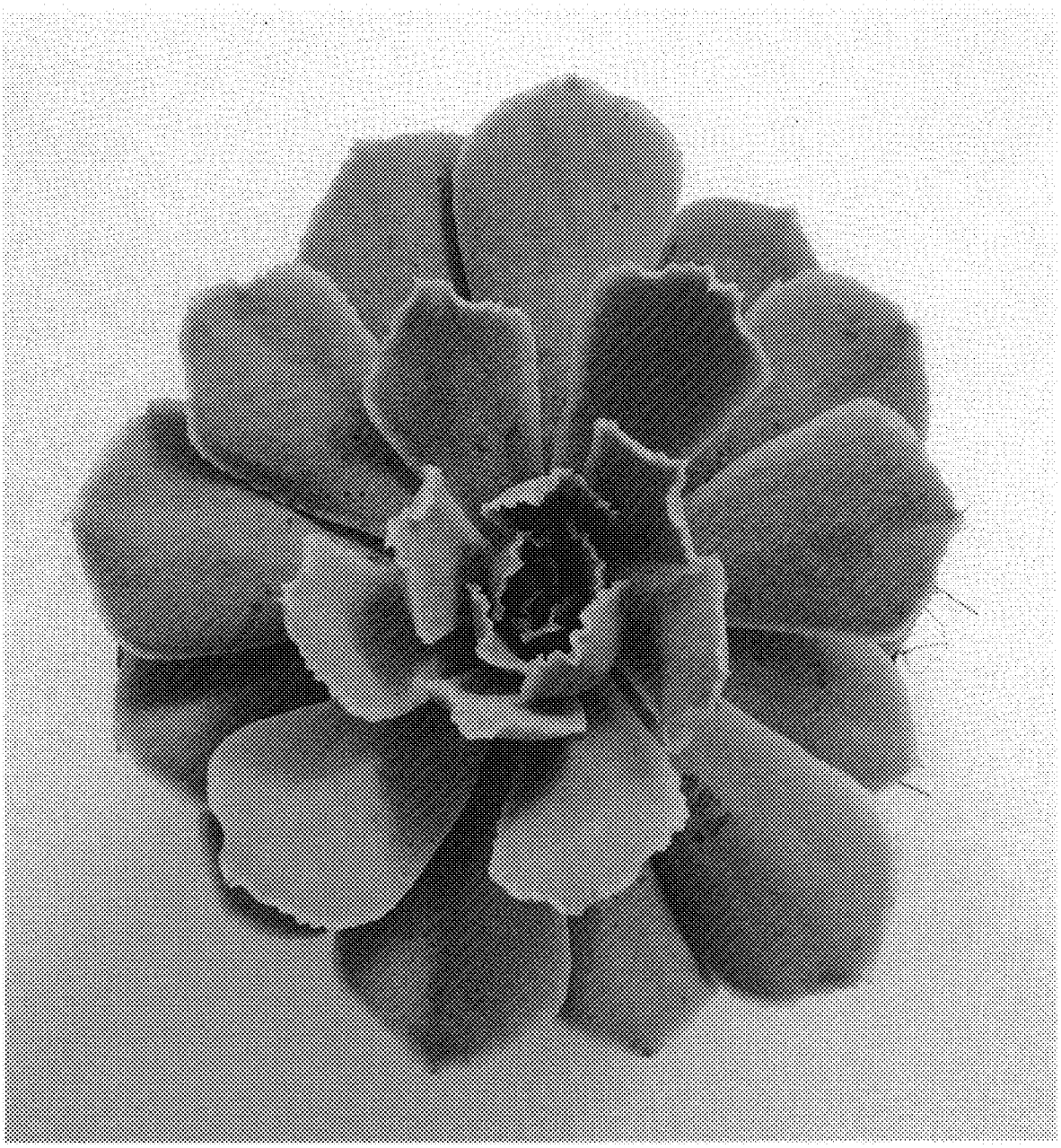
FIG. 2 illustrates, as nearly true as it is reasonably possible to make the same in color photographs of this type, the typical foliage arrangement of 'AMIECH2009'.
Figure 3:
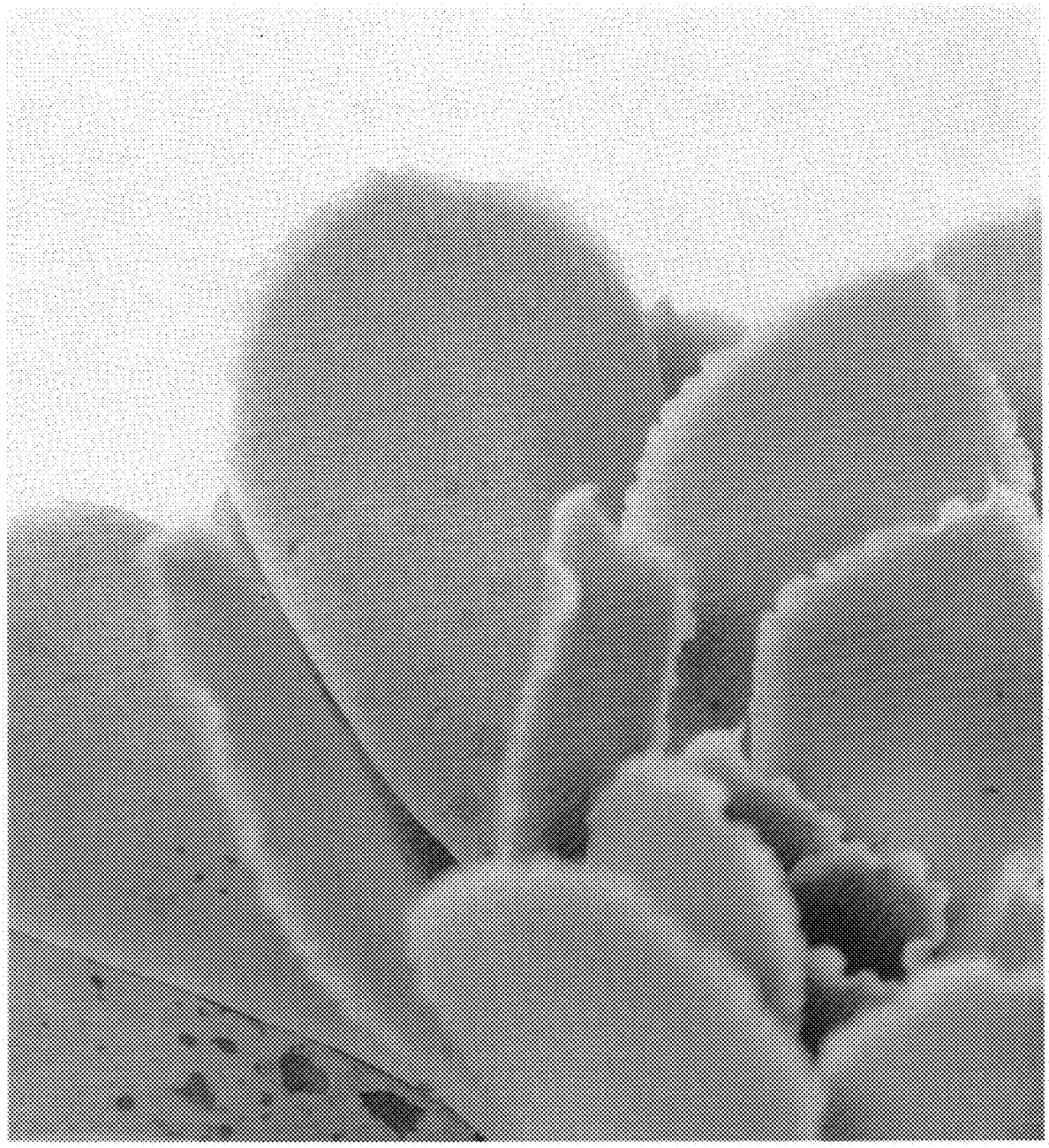
FIG. 3 illustrates, as nearly true as it is reasonably possible to make the same in color photographs of this type, the adaxial surface of the mature foliage 'AMIECH2009'.
Figure 4:
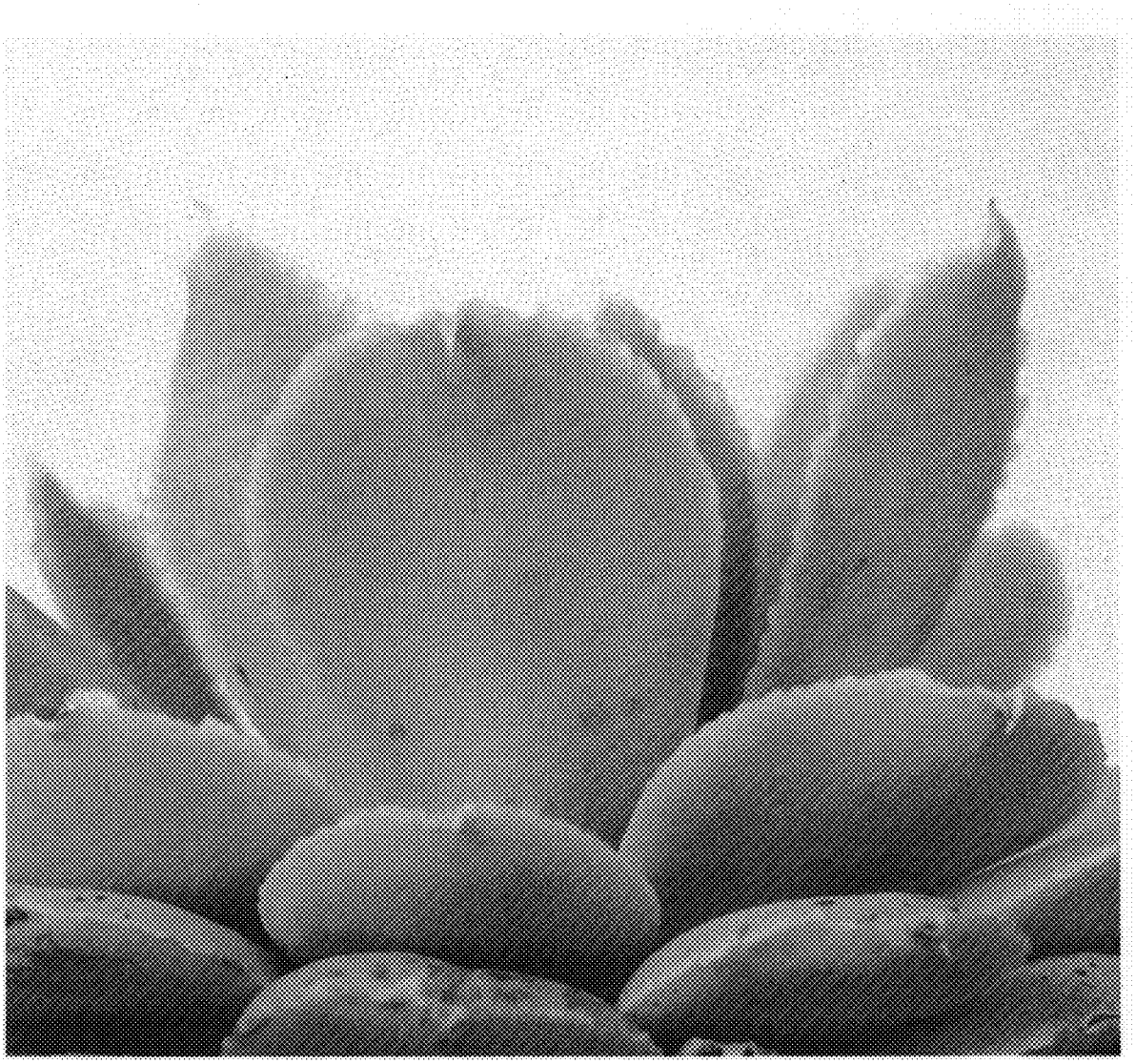
FIG. 4 illustrates, as nearly true as it is reasonably possible to make the same in color photographs of this type, the abaxial surface of the mature foliage 'AMIECH2009'.

The following observations and measurements made in June of 2021 describe averages from a sample set of six specimens of 25 week-old 'AMIECH2009' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2009' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2009' and comparisons with the parent plants and closest known comparator are provided below.

Plant description:

*Growth habit*.—Succulent perennial with foliage growing in a non-branched basal rosette.

*Plant shape*.—Flattened to flattened globular.

*Height from soil level to top of foliar plane*.—4.5 cm.

*Plant spread*.—Average of 12.1 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 40 leaves per rosette.

*Shape*.—Oblanceolate to narrowly obovate.

*Dimensions*.—5.1 cm long, 2.75 cm wide, and 0.5 cm thick, on average.

*Aspect*.—Flat.

*Attitude*.—Juvenile foliage at the center of the rosette is held upright; foliage becomes progressively more relaxed towards the outer whorls of mature foliage; mature foliage is held at approximately 30 degrees to horizontal.

*Apex*.—Obtuse to cuspidate.

*Base*.—Cuneate.

*Margin*.—Entire, proximally, and becoming crenulate towards the apex; margins are lightly to moderately undulate.

*Pubescence, texture and luster of the adaxial surface*.—Smooth, glabrous, and strongly glaucous.

*Pubescence, texture and luster of the abaxial surface*.—Smooth, glabrous, and strongly glaucous.

*Luster of the adaxial surface*.—Matte.

*Luster of the abaxial surface*.—Matte.

*Color*.—Juvenile foliage, adaxial surface — Green, nearest to RHS 143B, and narrowly margined with a translucent greyed-green, nearest to RHS 193D. The epicuticular glaucous wax covering the leaf surface is greyed-green, nearest to RHS 188A. Juvenile foliage, abaxial surface — Green, nearest to RHS 138B, and narrowly margined with a translucent greyed-green, nearest to RHS 193D. The epicuticular glaucous wax covering the leaf surface is greyed-green, nearest to RHS 188A. Mature foliage, adaxial surface — Yellow-green, nearest to a mixture of RHS 146A and 146B, and narrowly margined with a translucent greyed-green, nearest to RHS 193D. The epicuticular glaucous wax covering the leaf surface is greyed-green, nearest to RHS 188A. Mature foliage, abaxial surface — Yellow-green, nearest to a mixture of RHS 146B and 147B, and narrowly margined with a translucent greyed-green, nearest to RHS 193D. The epicuticular glaucous wax covering the leaf surface is greyed-green, nearest to RHS 188A. Venation, adaxial surface — No visible venation. Venation, abaxial surface — No visible venation.

*Petiole*.—No petiole; leaves are sessile.

Inflorescence : No flowering has been observed to date.

COMPARISONS WITH THE PARENT PLANTS AND CLOSEST KNOWN COMPARATOR

Plants of the new cultivar 'AMIECH2009' differ from the seed parent, an unnamed *Echeveria lilacina* plant (not patented), in the following characteristics described in Table 1 below.

TABLE 1

| Characteristic | 'AMIECH2009' | The seed parent. |
|---|---|---|
| Foliar margins. | Crenulate; lightly undulated. | Entire; not undulated. |
| General coloration of the foliage. | Pale greyed-green with a light cyanic hue. | Pale greyed-white and lightly to moderately suffused with red-purple; narrowly margined red-purple. |

Plants of the new cultivar 'AMIECH2009' differ from the pollen parent, an unnamed *Echeveria parva* plant (not patented), in the following characteristics described in Table 2 below.

TABLE 2

| Characteristic | 'AMIECH2009' | The pollen parent. |
|---|---|---|
| Foliar margins. | Crenulate; lightly undulated. | Entire; not undulated. |
| General coloration of the foliage. | Pale greyed-green with a slight cyanic hue. | In between very pale greyed-green to green-white; tipped greyed-red. |

COMPARISONS WITH THE CLOSEST KNOWN COMPARATOR

Plants of the new cultivar 'AMIECH2009' differ from the closest known commercial comparator, *Echeveria lilacina* 'OVPEARLS09' (not patented), in the following characteristics described in Table 3 below.

TABLE 3

| Characteristic | 'AMIECH2009' | 'OVPEARLS09' |
|---|---|---|
| Foliar margins. | Crenulated. | Entire. |
| Presence of globular growths on the abaxial foliar surface. | None present. | Present. |
| General coloration of the mature foliage. | Pale greyed-green with a slight cyanic hue. | A darker shade of greyed-green by comparison to 'AMIECH2009'. |
| Distal portion of the leaf margins. | Narrowly margined with a translucent greyed-green. | Conspicuously margined greyed-purple, generally appearing red. |

That which is claimed is:

1. A new and distinct variety of *Echeveria* hybrid plant named 'AMIECH2009', substantially as described and illustrated herein.

* * * * *